United States Patent
Wong et al.

[11] Patent Number: 5,854,391
[45] Date of Patent: Dec. 29, 1998

[54] GLYCOSYLATION OF PEPTIDES USING GLYCOSYL PHOSPHITE REAGENTS

[75] Inventors: Chi-Huey Wong, Rancho Santa Fe; Hirosato Kondo, San Diego, both of Calif.

[73] Assignee: The Scripps Research Institute, La Jolla, Calif.

[21] Appl. No.: 33,513

[22] Filed: Mar. 18, 1993

[51] Int. Cl.[6] .................................................. C07K 1/107
[52] U.S. Cl. .......................... 530/345; 530/340; 530/322
[58] Field of Search ........................ 514/23, 25; 530/333, 530/345

[56] References Cited

U.S. PATENT DOCUMENTS 4,719,289   1/1988   Kolar ...................................... 530/331

OTHER PUBLICATIONS

Martin *Tet Lett* 33 6123 1992.
Ichikawa *J Org Chem* 57, 2943, 1992.
Perich *Tet Lett* 29, 2369 (1988).
Garg, Adv. Carbohydr. Chem. Biochem. 43, 135, 1985.
Kunz, Angew Chem Int. Ed, 26, 294, 1987.
Watanabe, Synlett 115, 1993.
Galpin Chemistry in Britain 14, 181, 1978.
Paulsen, Org. Synth.: Interdiscip. Challenge Proc. IUPAC Symp. 5th (1985) 317–335.
Flowers, Methods Enzymol 138, 359–404.

*Primary Examiner*—Cecilia J. Tsang
*Assistant Examiner*—David Lukton
*Attorney, Agent, or Firm*—Donald G. Lewis

[57] ABSTRACT

A method for synthesizing glycosylated peptides employs a blocked carbohydrate donor and a blocked peptide acceptor. The carbohydrate donor includes an acid labile phosphite leaving group attached to the anomeric carbon. The blocked peptide acceptor includes an unprotected hydroxyl group susceptible to electrophilic attack. Serine hydroxyl is preferred. The reaction is initiated by the addition of a Lewis acid so as to activate the acid labile phosphite leaving group on the carbohydrate donor. The substitution reaction may be conducted at $-78°$ C. in a solvent such as $Et_3N$ which favors the formation of glycosylated peptide products.

5 Claims, No Drawings

GLYCOSYLATION OF PEPTIDES USING GLYCOSYL PHOSPHITE REAGENTS

GOVERNMENT RIGHTS

This invention was made with government support under Grant No. GM 44154 awarded by the National Institutes of Health. The U.S. government has certain rights in the invention.

FIELD OF THE INVENTION

The invention relates to the synthesis of O-linked glycopeptides. More particularly, the invention relates to a substitution reaction employing a carbohydrate donor having an acid labile phosphite and a blocked peptide acceptor having an unprotected hydroxyl group which is susceptible to electrophilic attack.

BACKGROUND OF THE INVENTION

Only a few side chains of the natural amino acid residues are known to be suitable for supporting glycosylation. The hydroxyl group of serine is known to glycosidically bond to mannose and to N-acetyl galactose; the hydroxyl group of threonine and of hydroxylysine are known to glycosidically bond to galactose; and the hydroxyl group of hydroxyproline is known to glycosidically bond to arabinose and to galactose. Additionally, the amide group of asparagine is known to form a glycosylamine bond with N-acetyl-glucosamine. The carboxyl groups of glutamic acid and aspartic acid are also known to be capable of forming ester bonds with carbohydrates.

The repertoire of naturally occurring glycopeptides is limited by the specificity the enzyme catalysis employed in their synthesis. What was needed to expand the repertoire of available glycopeptides was a broadly applicable method for their chemical synthesis.

SUMMARY

The invention is a substitution reaction employed for producing glycosylated peptide products. The substitution reaction employs a blocked carbohydrate donor and a blocked peptide acceptor. The blocked carbohydrate donor includes an anomeric carbon with an acid labile phosphite leaving group attached thereto. An example of a preferred blocked carbohydrate donor is dibenzyl 6-deoxy-2,3,4-tri-O-acetyl-β-L-galactopyranosyl phosphite. The acid labile phosphite leaving group is of a type which is activatable by a Lewis acid. An example of a preferred Lewis acid is trimethylsilyl trifluoromethanesulfonate (TMSOTf). A carbohydrate donor is considered to be "blocked" if it is unreactive with its activated form. The blocked peptide acceptor includes an unprotected hydroxyl group susceptible to electrophilic substitution. A peptide acceptor is considered to be "blocked" if it is unreactive with the activated carbohydrate donor except at the unprotected hydroxyl group. An example of a preferred peptide acceptor is N-benzyloxycarbonyl-L-alanyl-O-L-serine methyl ester. Other suitable peptide acceptors may include amino acid residues having a hydroxyl containing side chain, e.g. serine, threonine, hydroxylysine, and hydroxyproline. Various hydroxyl containing pseudopeptides may also be employed.

The carbohydrate donor and peptide acceptor are admixed in a solvent which promotes the formation of the substitution glycosylation reaction. An example of a preferred solvent is Et₃N. The reaction is initiated by the addition of the Lewis acid so as to activate the phosphite leaving group on the donor. The activated donor then reacts with the peptide acceptor by means of electrophilic attack to produce an O-glycosyl bond. After completion, the reaction is then quenched. Quenching may be achieved by washing the glycosylation products with saturated NaHCO₃.

The invention also includes glycosylated peptide products produced by the above synthetic method.

DETAILED DESCRIPTION

A scheme illustrating a glycopeptide reaction is provided below:

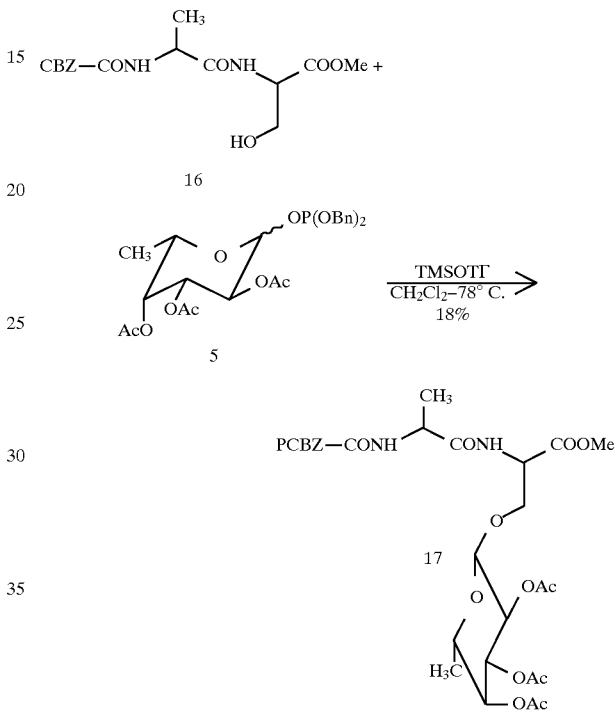

EXAMPLE

The blocked peptide acceptor, N-benzyloxycarbonyl-L-alanyl-L-serine methyl ester 16 (N-t-BOC-ALA-SER-methyl ester), was prepared according to conventional procedures. The carbohydrate donor, dibenzyl 2,3,4-tri-O-acetyl-L-fucosyl phosphite 5 was made according to the method of Ichikawa et al. (J. Org. Chem. 1992, 57, 2943). The blocked peptide acceptor 16 (32.4 mg, 0.1 mmol) and the carbohydrate donor 5 (53.4 g, 0.1 nmol) were admixed in 1 mL CH₂Cl₂ with molecular sieves of approximately 3Å and cooled to −78° C. The acid labile dibenzyl phosphite leaving group on the carbohydrate donor 5 was then activated by the addition of a Lewis acid, e.g. 9 mg, 0.040 mmol of trimethylsilyl trifluoromethanesulfonate (TMSOTf). After stirring the admixture for one hour at −78° C., the reaction was quenched with Et₃N and washed with saturated NaHCO₃. The organic solvents were dried over Na₂SO₄, filtered, and concentrated under reduced pressure.

The resultant residue was separated by preparative thin layer chromatography (Merck Art 5744, AcOEt/Hexane, 2:3) to give the glycosylated peptide product 17, i.e. N-benzyloxycarbonyl-L-alanyl-O-(6-deoxy-2,3,4-tri-O-acetyl-β-L-galactopyranosyl)-L-serine methyl ester. The yield was 18% (10 mg). The product 17 appeared as a colorless oil. If desired, the glycosylation product 13 may be deprotected to produce alanyl-O-(6-deoxy-2,3,4-tri-O-acetyl-β-L-galactopyranosyl)-L-serine.

The product 17 was subjected to NMR analysis, viz.: $^1$H-NMR (CDCL$_3$) δ; 1.22 (3H, d, J 6.4 Hz, Fuc—CH$_3$), 1.44 (3H, d, J 7.0 Hz, Ala—CH$_3$), 1.98, 2.04, 2.17 (3H, each s, OAc), 3.75 (3H, s, COOCH$_3$), 3.80 (1H, q, J 6.4 HZ, H-5), 4.05 (2H, bd, J 2.28 Hz, Ser—Ch$_2$), 4.31 (1H, t, J 7.0 Hz, Ala—CH), 4.39 (1H, d, J 7.8 Hz, H-1), 4.723 (1H, dt, J 2.8, 8.4 Hz, Ser—CH), 4.99 (1H, dd, J 3.44, 10.5 Hz, H-3), 5.09–5.13 (3H, m, H-2 and benzyl protons), 5.22(1H, dd, J 0.96, 3.44 Hz, H-4), 5.46 (1H, d, J 7.0 Hz, CONH), 6.69 (1H, d, J 8.44 Hz, CONH), 7.31–7.37 (5H, m, phenyl protons).

HRMS: Calclated for $C_{27}H_{36}N_2O_{13}Cs$ (M+Cs$^+$) 729.1272; found value was 729.1276.

What is claimed is:

1. A method for glycosylating peptides comprising the following steps:

Step A: providing a blocked carbohydrate donor having an anomeric carbon with an acid labile phosphite leaving group attached thereto;

Step B: blocking a peptide for providing a blocked peptide acceptor including an amino acid residue having an unprotected hydroxyl group, the amino acid residue being selected from a group consisting of serine, threonine, hydroxylysine, hydroxyproline, and hydroxyl containing pseudopeptides;

Step C: providing a promotor having Lewis acid activity for catalyzing the phosphite leaving group of said Step A; then Step D: reacting the blocked carbohydrate donor of said Step A with the blocked peptide acceptor of said Step B in the presence of the promotor of said Step C within a solvent favoring the formation of glycosylated peptide products; and then Step E: quenching the reaction of said Step D.

2. A method for glycosylating peptides as described in claim 1 wherein:

in said Step B, the peptide acceptor is N-benzyloxycarbonyl-L-alanyl-O-L-serine methyl ester.

3. A method for glycosylating peptides as described in claim 1 wherein:

in said Step C, the promotor is trimethylsilyl trifluoromethanesulfonate (TMSOTf).

4. A method for glycosylating peptides as described in claim 1 wherein:

in said Step E, quenching is achieved by the addition of Et$_3$N and is followed by washing the glycosylation products with saturated NaHCO$_3$.

5. A method for glycosylating peptides as described in claim 1 wherein:

in said Step A, the phosphite leaving group is dibenzyl phosphite.

* * * * *